(12) United States Patent
Mahn

(10) Patent No.: US 9,603,682 B2
(45) Date of Patent: Mar. 28, 2017

(54) METHOD AND SYSTEM OF MAKING DENTAL IMPRESSIONS

(71) Applicant: Mark Mahn, Paris (CA)

(72) Inventor: Mark Mahn, Paris (CA)

(*) Notice: Subject to any disclaimer, the term of this patent is extended or adjusted under 35 U.S.C. 154(b) by 135 days.

(21) Appl. No.: 14/572,866

(22) Filed: Dec. 17, 2014

(65) Prior Publication Data

US 2015/0173867 A1 Jun. 25, 2015

Related U.S. Application Data

(60) Provisional application No. 61/935,469, filed on Feb. 4, 2014, provisional application No. 61/918,842, filed on Dec. 20, 2013.

(51) Int. Cl.
*A61C 9/00* (2006.01)

(52) U.S. Cl.
CPC .............. *A61C 9/0006* (2013.01); *A61C 9/00* (2013.01)

(58) Field of Classification Search
CPC .................................. A61C 9/0006; A61C 9/00
See application file for complete search history.

(56) References Cited

U.S. PATENT DOCUMENTS

| | | | | |
|---|---|---|---|---|
| 4,483,675 A * | 11/1984 | Marshall | .................. | A61C 9/00 433/141 |
| 5,676,543 A * | 10/1997 | Dragan | ................ | A61C 9/0033 433/136 |
| 2002/0055082 A1* | 5/2002 | Durbin | .................... | A61C 9/00 433/29 |
| 2002/0193502 A1* | 12/2002 | Hare | ....................... | A61K 6/10 524/588 |
| 2009/0075240 A1* | 3/2009 | Discko, Jr. | ........... | A61C 9/0033 433/215 |
| 2009/0274999 A1* | 11/2009 | Coopersmith | ....... | A61C 8/0001 433/218 |

* cited by examiner

*Primary Examiner* — Robert N Wieland

(57) ABSTRACT

The present invention is a method of making a dental impression, having the first step of providing an impression tray filled with a first high viscosity impression material. The second step is to take a first impression by inserting the tray into the patient's mouth over a prepared tooth for the patient to bite and let cure. Thirdly, the tray is removed and a second low viscosity impression material is applied over the prepared tooth. The tray is then reinserted into the mouth over the prepared tooth of the patient in order to take a second impression of the prepared tooth, allowing the hydraulic pressure created by the second impression material to urge the sulcus away from the tooth margin. At this point, the tray is removed from the patient's mouth.

19 Claims, 15 Drawing Sheets

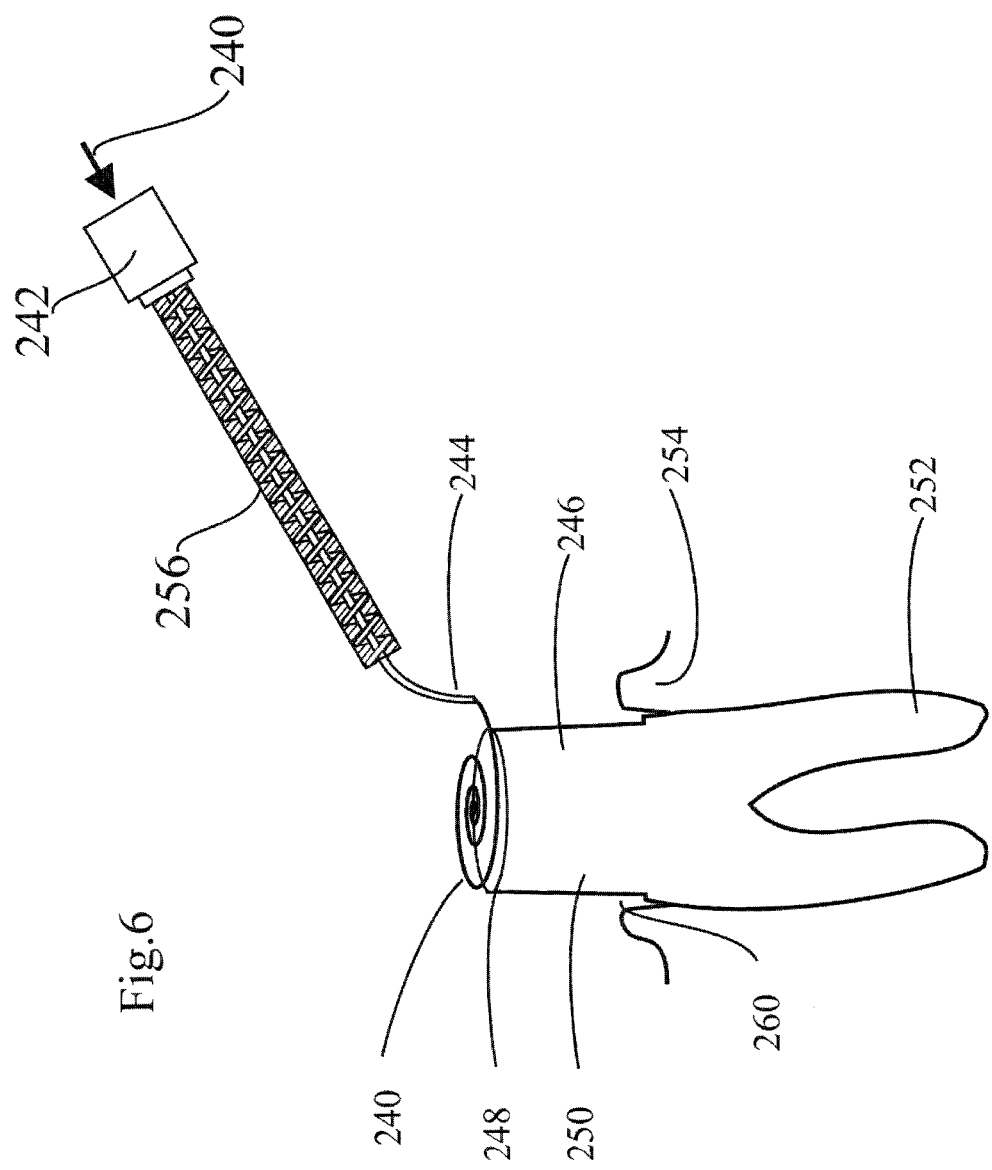

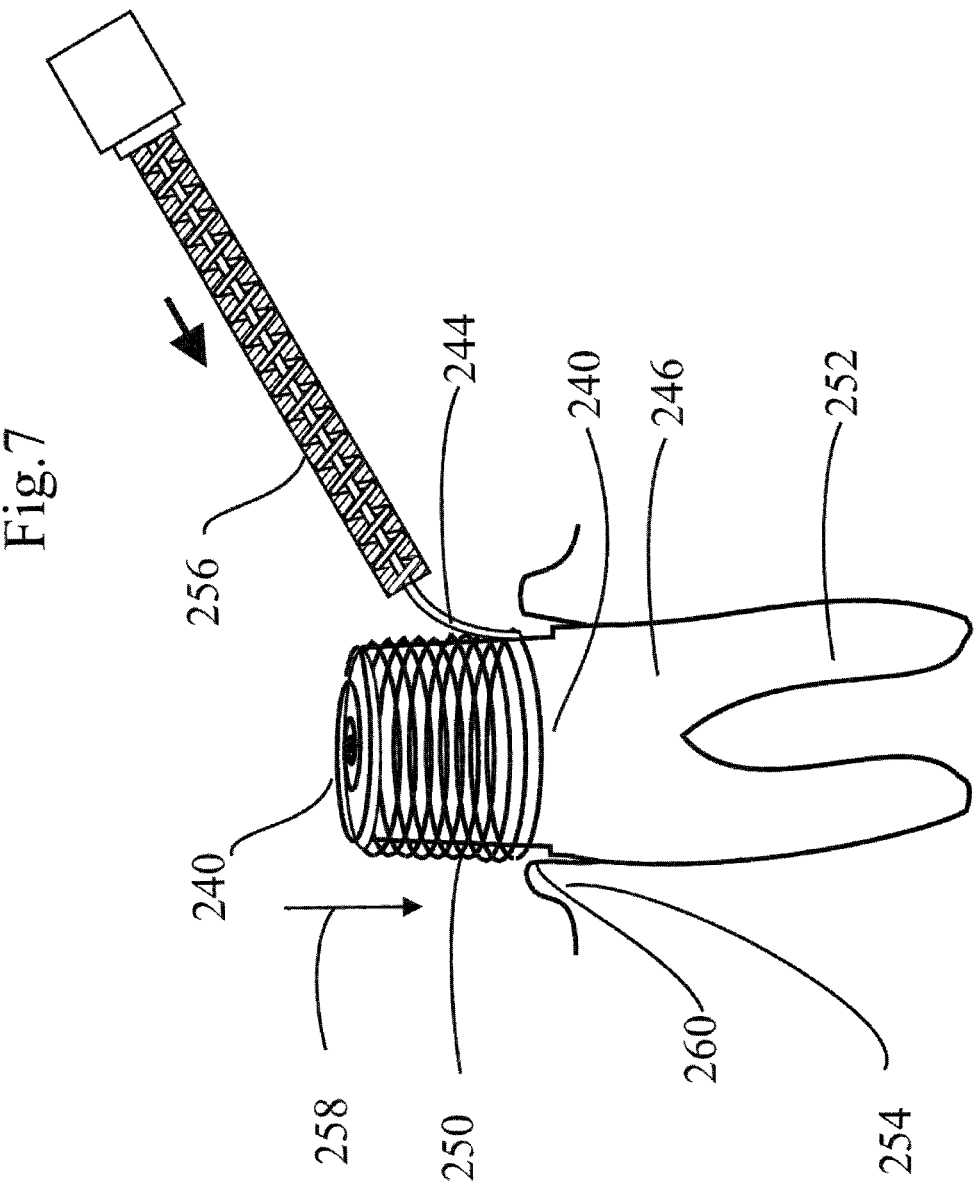

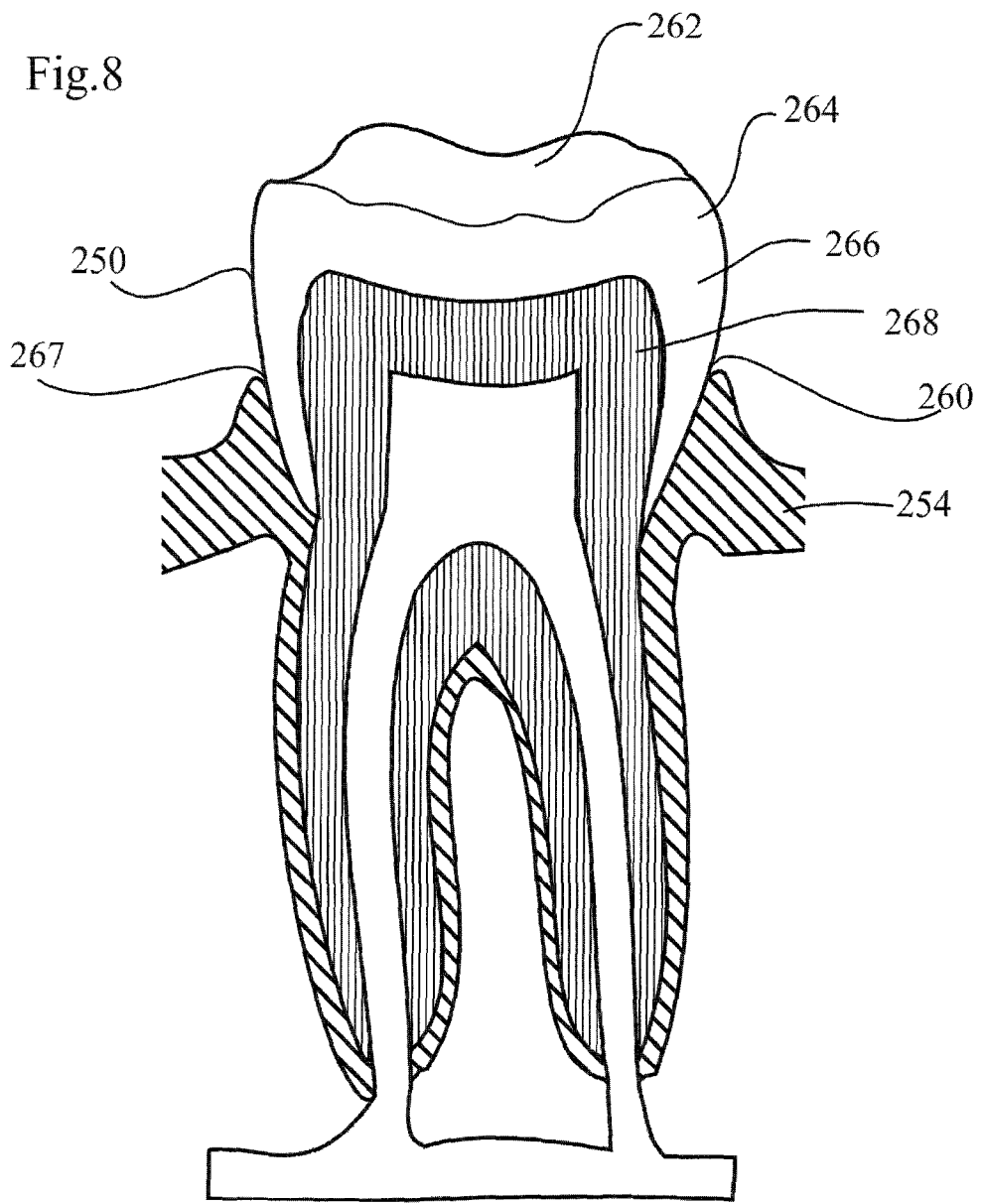

Impression Method

Application of second impression material

METHOD AND SYSTEM OF MAKING DENTAL IMPRESSIONS

This application claims priority from previously filed provisional application 61/935,469, filed by Mark Mahn on Feb. 4, 2014, under the title METHOD AND SYSTEM OF MAKING DENTAL IMPRESSIONS, which claims priority from previously filed provisional application 61/918,842, filed by Mark Mahn on Dec. 20, 2013, under the title METHOD AND SYSTEM OF TAKING DENTAL IMPRESSIONS.

FIELD OF THE INVENTION

The present concept relates to a method and system of making dental impressions and more particularly relates to the method and system of making dental impressions for the purpose of manufacture of crowns, veneers and bridges in dental laboratories.

BACKGROUND OF THE INVENTION

Currently there are a number of different methods being used by dentists to create dental impressions which are ultimately used for the manufacture of crowns, veneers, and bridges.

For example a crown is a type of dental restoration which completely caps and encircles the tooth or dental implant. They are typically bonded to the tooth using a dental cement and are usually fabricated outside of the mouth in order that they can be made of strong material such as gold or ceramics.

The most common method of crowning a tooth usually involves a dental impression of a prepared tooth by a dentist for fabrication of the crown outside of the mouth. The crown can then be inserted at a subsequent dental appointment. Naturally the tooth to restoration margin is an unsightly thing to have exposed on the visible surface of the tooth when the tooth is positioned in the aesthetic zone of a smile. The dentist would like to place the margin as far toward the gum line as possible and even below the gum line.

In order to obtain impressions below the gum line typically a gingival retraction cord is placed around the tooth at the sulcus in order to push the gum away from the margin of the tooth at the gingival sulcus. In this manner it is possible to take a dental impression which extends below the gum line.

The difficulties with this technique are that there is a lot of trauma and damage to the gum at the gingival sulcus interface which usually results in bleeding during the procedure.

The blood and other fluids interfere with the impression material that is being used when making the impressions to have a crown manufactured.

Typically a vinyl polysiloxane impression material is used to take the impression of the prepared tooth. Typically one impression is taken and sent to the laboratory for manufacture of the crown.

Unfortunately there is variation amongst dental offices and the materials that they are using. Some dental office prefer to use a heavy impression material whereas other dental offices prefer to use a more light body meaning less viscous impression material. Some dental offices prefer to use a hydrophilic whereas other dental offices do not prefer hydrophilic materials. Some dental offices prefer to use triple trays as they are known in the industry for making an impression whereas other dental offices prefer other tray configurations.

So there is a great deal of inconsistency among dental offices which results in inconsistent accuracy of the impressions which the laboratory eventually has to deal with.

As a result there is a large degree of scrap in the manufacture of crowns which do not fit or require a lot of rework on the part of the dentist in order to make them fit properly onto the prepared tooth.

Other systems have also been unsuccessfully suggested, such as that described in U.S. Pat. No. 6,116,905 titled METHOD OF TAKING DENTAL IMPRESSIONS invented by Jeffrey C. Hoos. None of these other systems utilize hydraulic pressure to move the sulcus or apply impression material directly to the prepared tooth.

Therefore there is a need for a method and system of making dental impressions which provides for a uniform and reproducible dental impression which can be used by the laboratory to produce a uniform and consistent crown quality.

SUMMARY OF THE INVENTION

The present concept is a method of making a dental impression, the method comprising:
  a) providing an impression tray, a first high viscosity impression material, wherein the impression tray is filled with the first impression material;
  b) take a first impression by inserting the tray into the mouth over a prepared tooth for the patient to bite and let cure;
  c) remove the tray and apply a second low viscosity impression material over the prepared tooth and reinsert tray into the mouth over the prepared tooth of patient to bite and let cure;
  d) remove the tray from the mouth of the patient.

Preferably further including the step c' prior to step c as follows:
  c') tracing the sulcus of the prepared tooth with an instrument to separate the sulcus from the tooth.

Preferably further including the step c' prior to step c as follows:
  c') rinsing thoroughly the prepared tooth and tracing the sulcus of the prepared tooth with an explorer instrument to separate the sulcus from the tooth.

Preferably including the step e after the step d as follows:
  e) diagnose the quality of the impression.

Preferably wherein in step c a layer of second impression material is applied over the prepared tooth starting at the coronal portion of the prepared tooth.

Preferably wherein in step c a layer of second impression material is applied over the prepared tooth starting at the coronal portion of the prepared tooth and proceeding downwardly along the side surfaces of the tooth to the sulcus Preferably wherein in step c a thin layer of second impression material is applied over the prepared tooth in a continuous circular motion starting at the coronal portion of the prepared tooth and proceeding downwardly around the side surfaces of the tooth to the sulcus.

Preferably wherein in step a the first impression material is a hydrophilic polysiloxane impression material.

Preferably wherein in step a the first impression material is a first colored impression material.

Preferably wherein in step c the second impression material is a hydrophilic polysiloxane impression material.

Preferably wherein in step c the second impression material is a second colored impression material.

Preferably wherein in step c the second impression material is a second colored impression material contrasting with the first colored impression material.

Preferably wherein in step c the second impression material is a second colored impression material.

Preferably wherein in step c the second impression material is a second colored impression material contrasting with the first colored impression material.

Preferably wherein in step a the tray is a triple tray.

Preferably wherein step c is replaced with the following step c' as follows:

c) remove the tray and trim back excess first impression material and apply a second low viscosity impression material over the prepared tooth and reinsert tray into the mouth over the prepared tooth of patient to bite and let cure.

Preferably wherein step c is replaced with the following step c' as follows:

c) remove the triple tray and trim back excess first impression material to about the top of the vertical walls of the impression tray and apply a second low viscosity impression material over the prepared tooth and reinsert tray into the mouth over the prepared tooth of patient to bite and let cure.

Preferably wherein step e is replaced with the following step e) diagnose the quality of the impression by observing the colouring of the impression.

Preferably wherein step e is replaced with the following step e) diagnose the quality of the impression by observing the colouring of the impression and reject the impression if second impression material is observed anywhere other than the sulcus area of the prepared tooth.

Preferably wherein step e is replaced with the following step e) diagnose the quality of the impression by observing the definition of the tooth impression.

Preferably wherein step e is replaced with the following step e) diagnose the quality of the impression by observing the definition of the tooth impression and reject the impression if sharply defined fin like structures in the sulcus area of the prepared tooth are not present.

BRIEF DESCRIPTION OF THE DRAWINGS

The present concept will now be described by way of example only with reference to the following drawings in which:

FIG. 6 is a schematic plan view of a prepared tooth with the top or coronal portion of the tooth being covered with second impression material using a circular motion.

FIG. 7 is a schematic plan view of a prepared tooth showing the side surfaces of the tooth being covered by a second impression material in a circular motion.

FIG. 8 is a schematic cross sectional view of a healthy tooth showing the tooth and the gum interfaces.

DETAILED DESCRIPTION OF THE PREFERRED EMBODIMENTS:

Definitions

Step 1 material or first impression material=high viscosity (heavy) hydrophilic impression material preferably a two part polysiloxane having a first colour.

Step 2 material or second impression material =low viscosity (light) hydrophilic impression material, preferably a two part polysiloxane, having a second colour contrasting to the first colour.

Dental impression: A negative imprint of hard (teeth) and soft tissues in the mouth from which a positive reproduction (or cast) can be formed for use in restorative dentistry for crowns, bridges, veneers and implants for example.

Hemostasis: the stopping of a flow of blood.

Astringent: a chemical agent causing the contraction of body tissues, typically of the skin.

Gingival retraction: lateral movement of the gingival margin away from the tooth surface. It is usually termed gingival retraction as an intentional procedure, and in such cases it is traditionally performed by mechanical, chemical or electrical means in order to perform certain dental surgery procedures.

Triple tray: is also known as a dual arch tray and are one and the same.

Description

Figure 12:
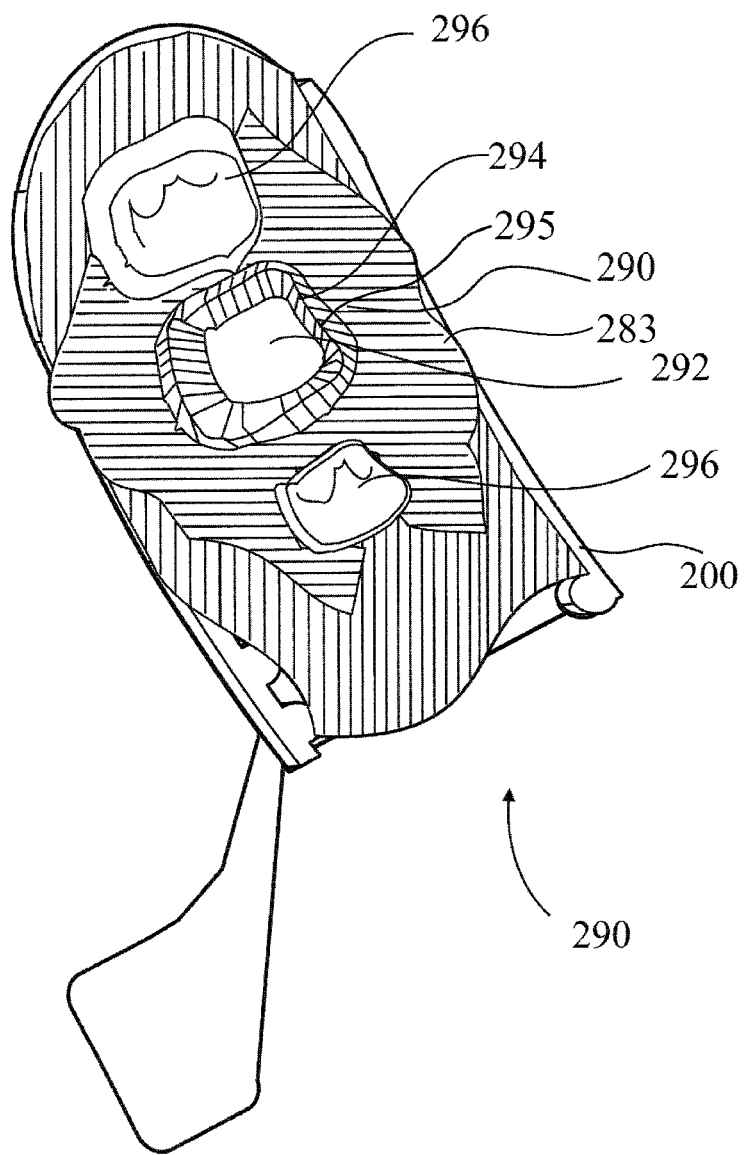
FIG. 12 is a top perspective view of a posterior triple tray showing cured and completed first and second tooth impressions.
Figure 13:
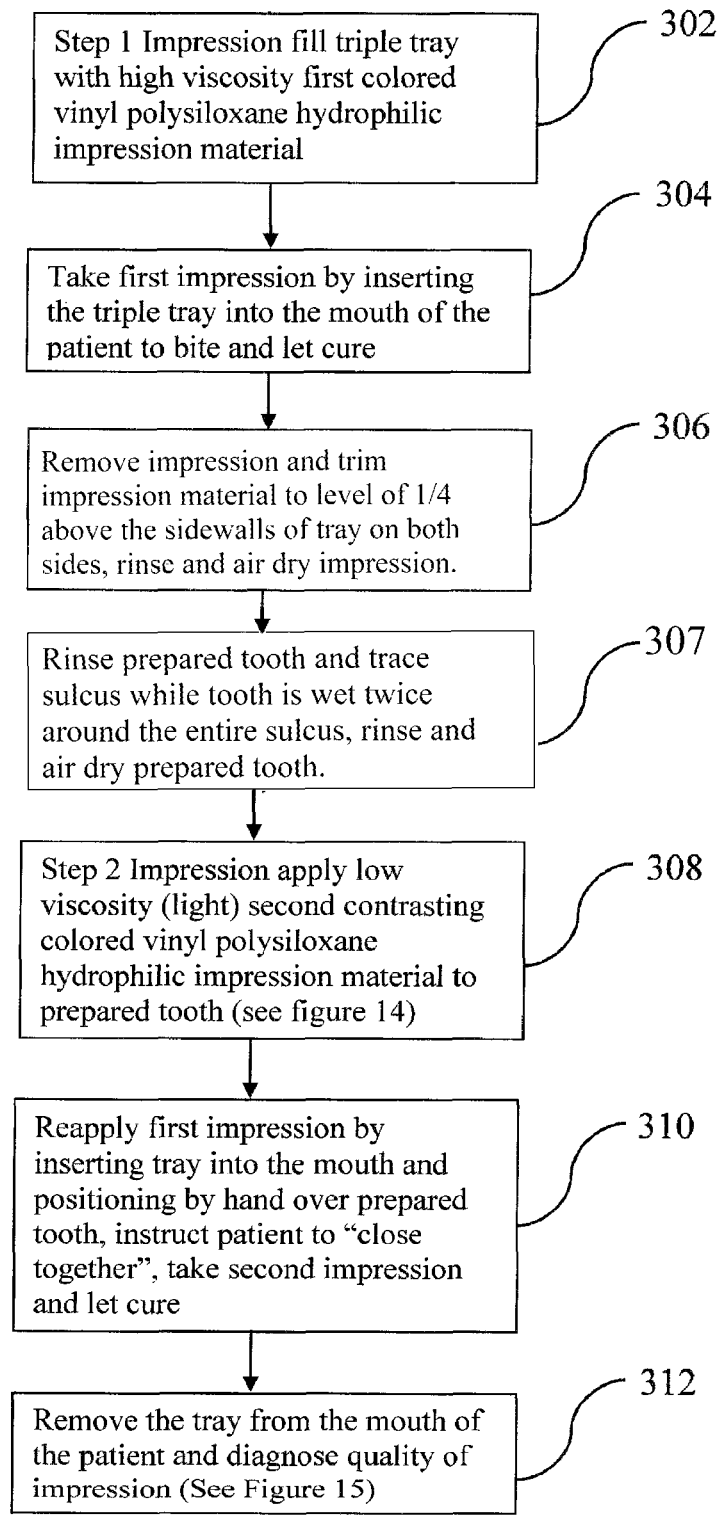
FIG. 13 is a flow diagram depicting the steps of the impression method.
Figure 14:
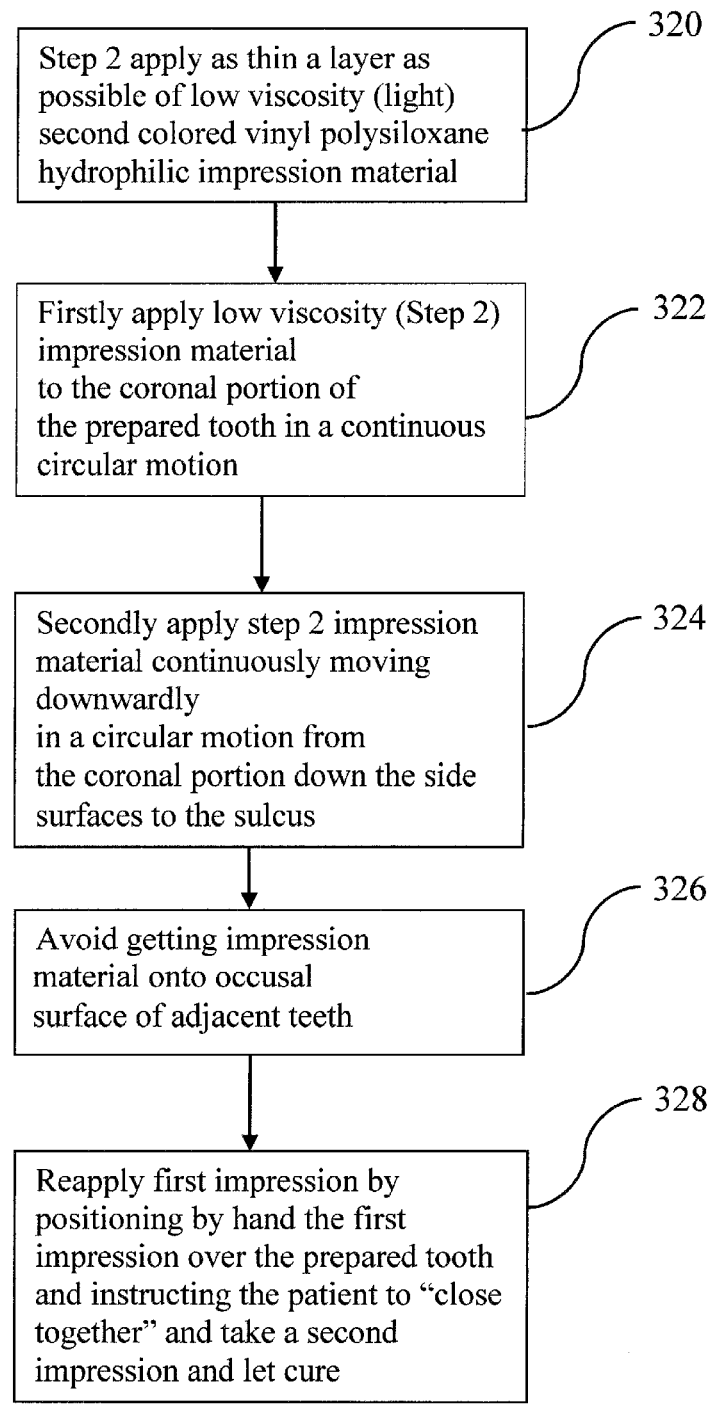
FIG. 14 is a flow diagram showing the steps of the second impression.

The present concept a method and system of making dental impressions is shown in FIGS. 1 through 14 and particularly the method of making dental impressions is shown more particularly in FIGS. 13 and 14.

FIG. 8 is a schematic cross sectional view of a healthy tooth showing the portions of the tooth namely the crown 264 which includes occlusal surface 262 and crown side surfaces 250, the enamel 266, the dentin 268, the gingival sulcus interface 260, the gum 254 and the tooth margin 267.

Figure 9:
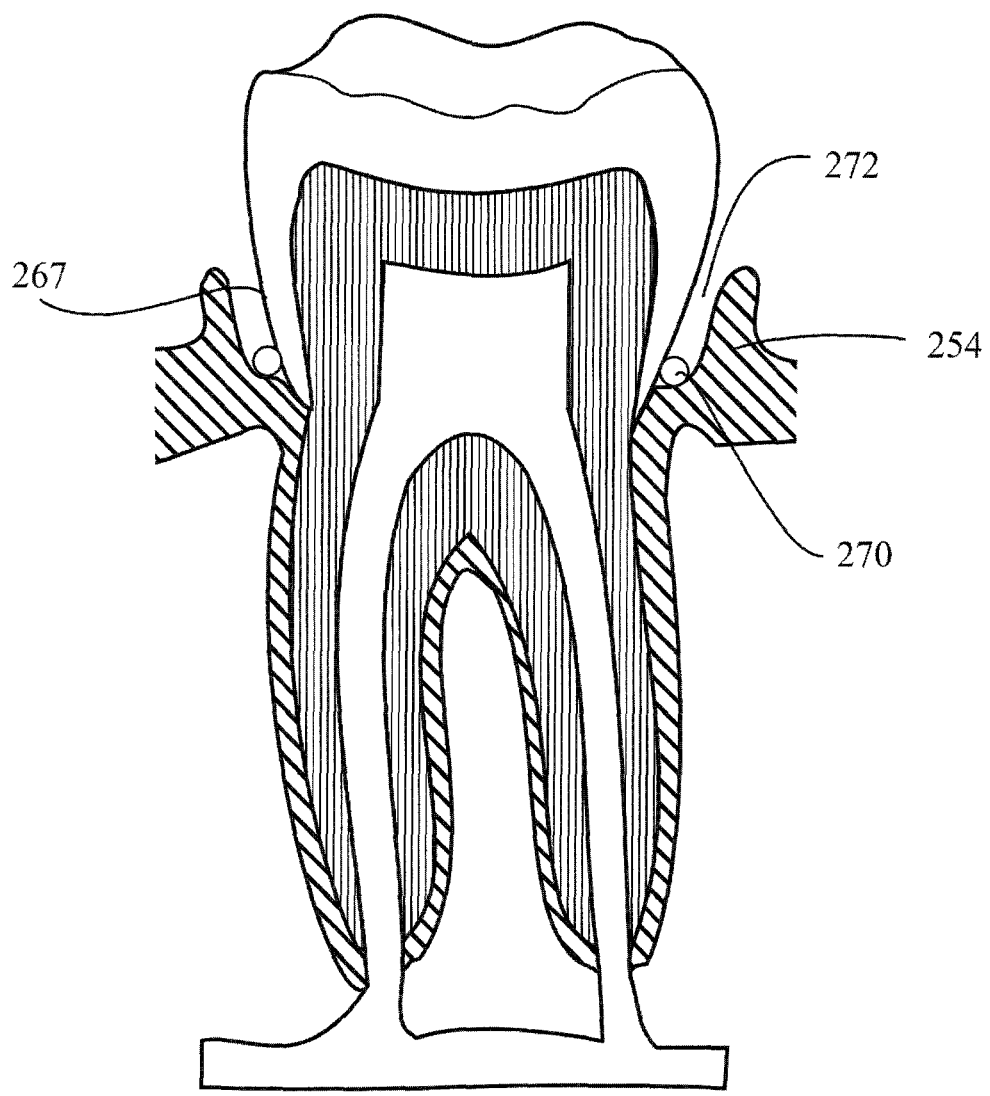
FIG. 9 is a schematic cross sectional view of a tooth showing a gingival retraction cord in place in order to expose the tooth margin below the gum line.

FIG. 9 shows a cross sectional schematic view of the gums 254 being retracted using the gingival retraction cords 270 in accordance with known prior art procedures. The cords 270 are pushed into the gingival sulcus gap 272 at tooth margins 267 thereby retracting gum 254 away from the tooth margins 267. This process often causes significant bleeding and trauma to the gums. The presently invented process does not use any retraction cords to make the dental impressions.

Referring now to FIG. 13 the method of making dental impressions includes the following steps:

Step 1 impression, fill triple tray with high viscosity (heavy) first colored vinyl polysiloxane hydrophilic impression material shown as 302.

Take first impression and let cure shown as 304.

Figure 5:
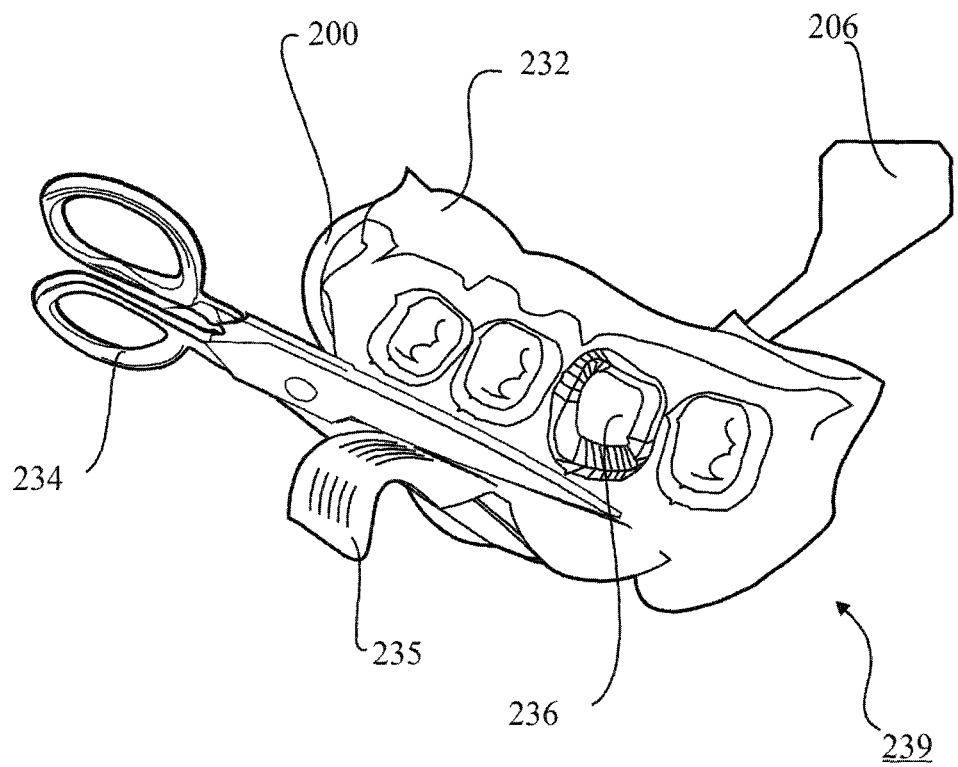
FIG. 5 is a schematic top perspective view of a posterior triple tray with cured first impression material showing first impressions of teeth therein and the excess impression material being cut away with scissors.
Figure 5A:
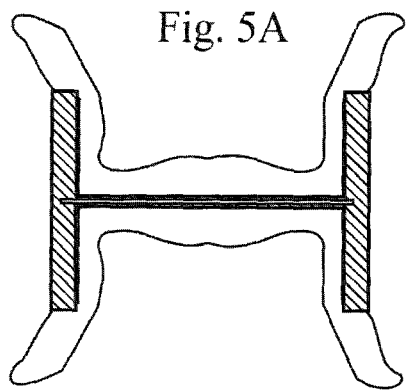
FIG. 5A is a cross sectional schematic view taken along lines 4-4 of FIG. 4 showing in cross section of the posterior triple tray with cured first impression material with excess impression material present.
Figure 5B:
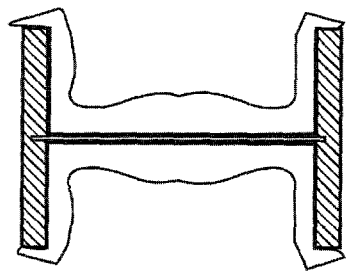
FIG. 5B is a cross sectional view taken along lines 4-4 of FIG. 4 showing in cross section of the posterior triple tray after trimming off the excess impression material.

Remove impression and trim impression material to level of ¼" above the sidewalls of tray, on both sides of tray and rinse and air dry impression as shown as 306 and also in FIGS. 5, 5A & 5B.

Rinse prepared tooth and trace sulcus while tooth is wet twice around the entire sulcus, rinse and air dry prepared tooth as shown in 307.

Step 2 impression apply low viscosity (light) second contrasting colored vinyl polysiloxane hydrophilic impression material to prepared tooth shown as 308 and which is described more fully in FIG. 14.

Reapply first impression, by positioning by hand over the prepared tooth the first impression and instruct patient to "close together" take second impression and let cure shown as 310.

Figure 15:
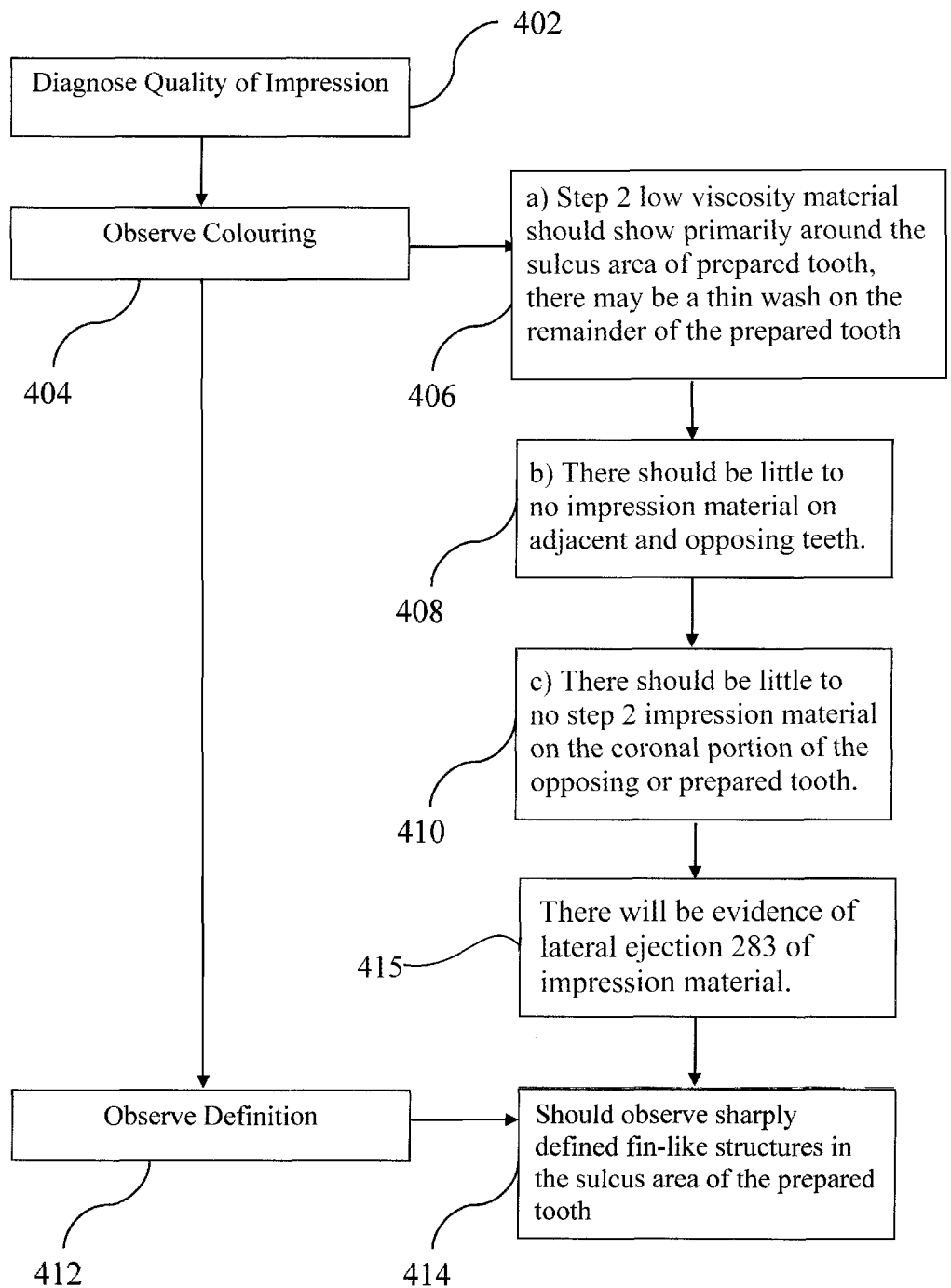
FIG. 15 is a flow diagram showing the steps of diagnosing the quality of the impression.

Diagnose quality of impression as shown as 312, the process described more fully in FIG. 15.

Further details in regard to application of the second colored vinyl polysiloxane hydrophilic impression material is detailed in FIG. 14 as follows:

Step 2 apply as thin a layer as possible of low viscosity (light) second colored vinyl polysiloxane hydrophilic impression material shown as 320.

Firstly apply low viscosity step 2 impression material to the coronal portion of the prepared tooth in continuous circular motions shown as 322.

Secondly apply step 2 impression material continuously moving downwardly in a circular motion from the coronal portion down the side surfaces to the sulcus shown as 324.

Avoid getting impression material onto occlusal surface of adjacent teeth shown as 326.

Reapply first impression and take a second impression and let cure shown as 328. The patient in this step is instructed to "close together" or "bite together" and not to squeeze or squeeze hard to avoid distortions in mouth or triple tray alignment material.

Referring now to FIG. 15 of the method of diagnosing quality of impression 402 include the following steps:

Observe colouring of the final impression for the following characteristics shown as 404.

Step 2 low viscosity material should show primarily around the sulcus area of prepared tooth, although there may be a thin wash on the remainder of the prepared tooth, shown as 406.

There should be little to no impression material on adjacent or opposing teeth, shown as 408.

There should little to no step 2 impression material on the coronal portion of the opposing or prepared tooth, shown as 410.

There will be evidence of lateral ejection 283 of step 2 impression material from the prepared tooth, shown as 410 and also in FIG. 12. This will indicate that there has been adequate cover and pressure release for step 2 material.

Observe definition of the final impression for the following characteristics, shown as 412.

Should observe sharply defined fin-like structures in the sulcus area of the prepared tooth, shown as 414.

Figure 1:
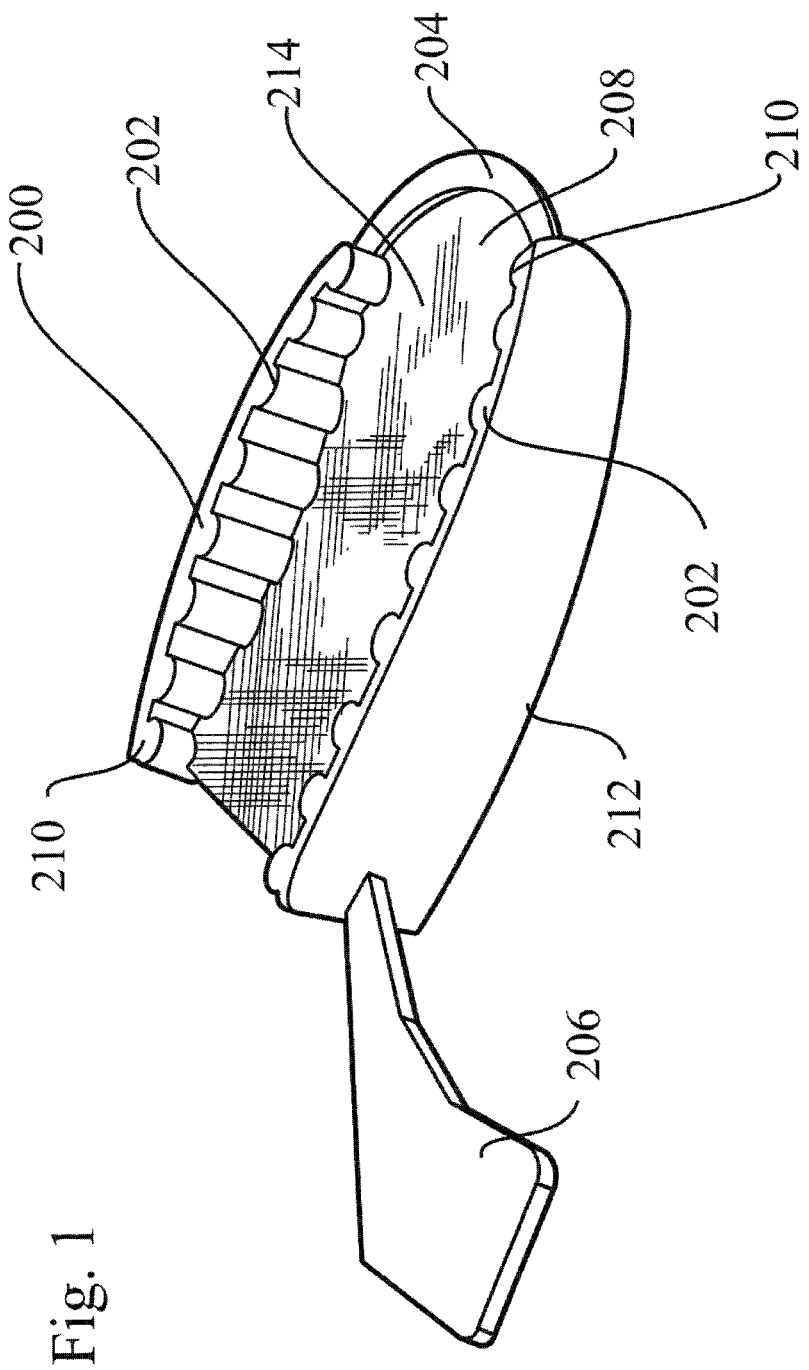
FIG. 1 is a schematic top perspective view of a posterior triple tray which is used in the process of making dental impressions.

Referring now to FIG. 1 which is a schematic top perspective view of a posterior triple tray 200 which includes two side walls 202 connected with a connector 204 and having a handle 206 attached thereto and a screen 208 running through the centre of each sidewall 202 and across the posterior triple tray 200 as shown in FIG. 1.

Posterior triple tray 200 further includes top edge 210 on the top side 214 of posterior tray 200 and bottom edge as 212 and each of the side walls 202 on the bottom side of the posterior triple tray which is not shown.

Note that the bottom side of the posterior triple tray 200 not shown is a mirror image of the top side as shown in FIG. 1.

Figure 2:
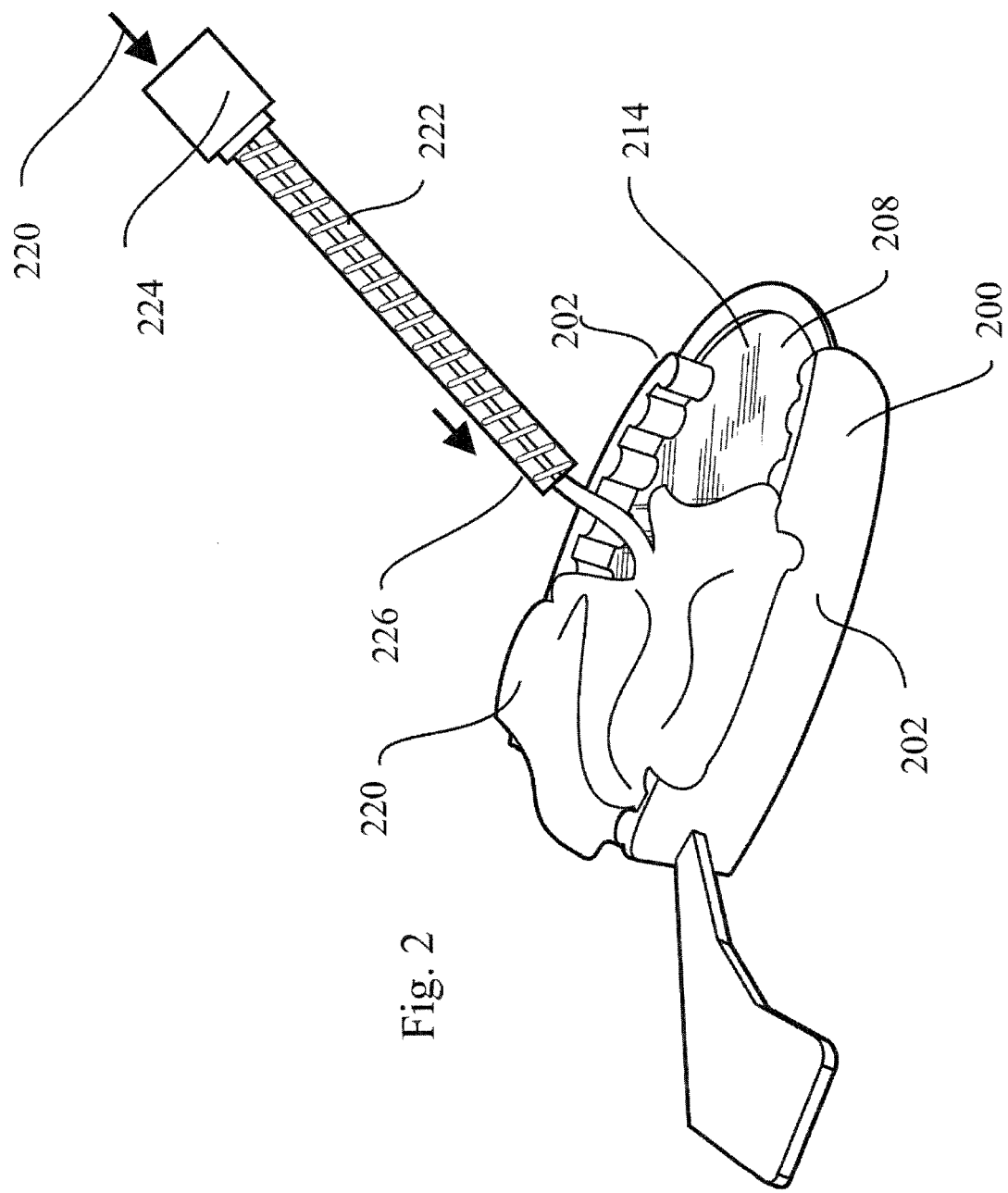
FIG. 2 is a schematic perspective top view of a posterior triple tray being filled with a heavy first impression material.

In use the top and bottom of posterior triple tray 200 is filled with heavy step 1 hydrophilic first impression material and is shown in FIG. 2 meaning a more viscous first impression material 220 is applied via a mixing nozzle 222 which has an entry end 224 and an exit end 226 and is applied to the top side 214 of screen 208 thereby filling up the gap between the two side walls 202 of posterior triple tray 200.

Inevitably there will be excess first impression material 220 and this should be smoothed down typically by using the mixing nozzle 224 and running it across the top edges 210 and bottom edges of triple tray 200 thereby smoothing out the first impression material squeezed onto the triple tray.

Figure 4:
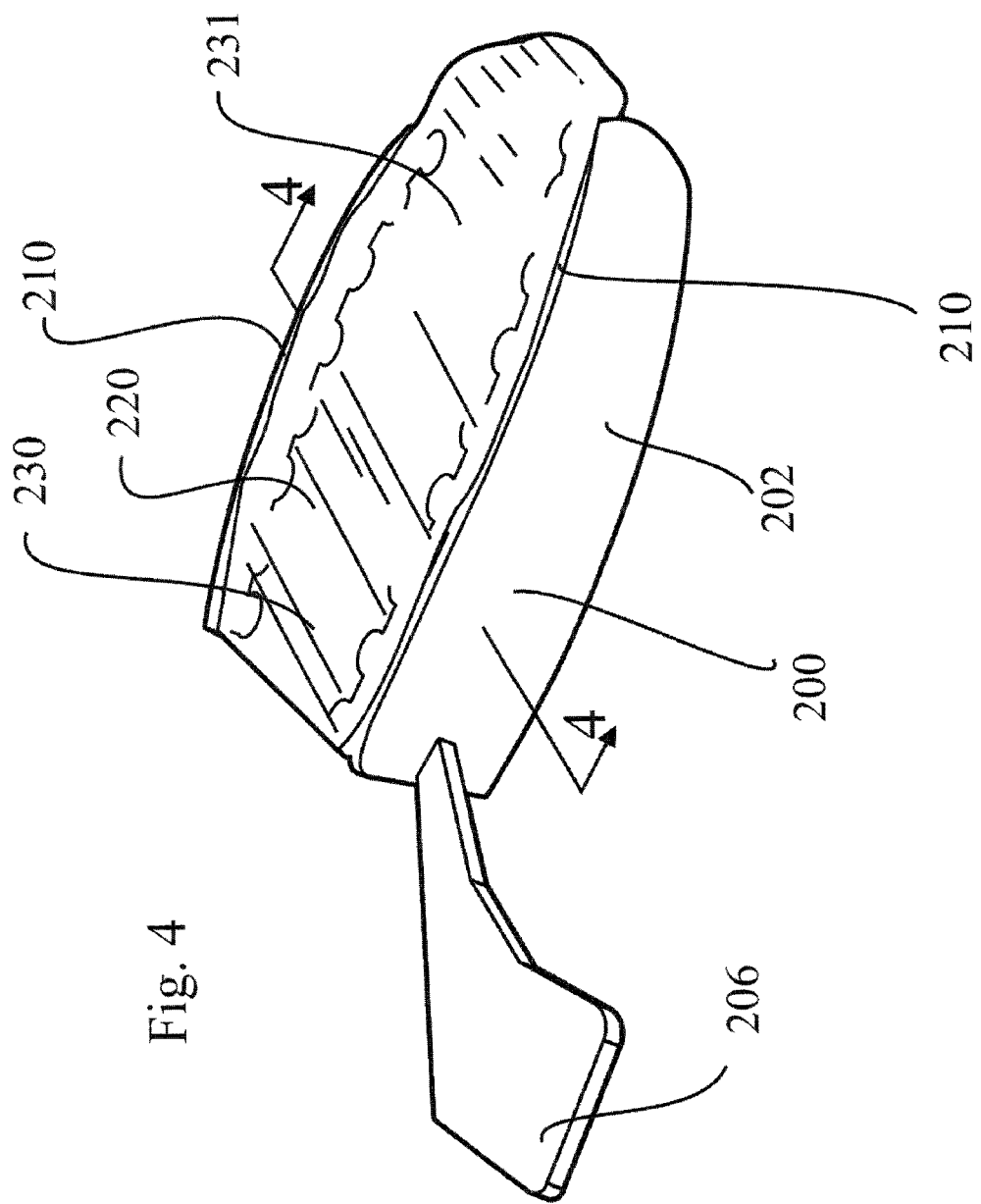
FIG. 4 is a schematic top perspective view of a posterior triple tray filled with uncured first impression material ready for placement into the mouth.

FIG. 4 is a schematic perspective top view of a triple tray showing first impression material 220 having a smooth surface 231 created by smoothing first impression material with the mixing nozzle 222. FIG. 4 depicts posterior triple tray 200 in the ready to use condition with uncured impression material 230 positioned in posterior triple tray 200.

FIG. 5 is a schematic top perspective of posterior triple tray 200 showing a cured first impression material 232 with a first impression 236 taken of the prepared tooth wherein scissors 234 are used to cut away excess impression material 235 beyond the tray walls which has oozed out of the posterior triple tray 200 during making of the impression. FIG. 5A show the excess impression material before trimming and FIG. 5B show the excess impression material after being trimmed away.

FIGS. 1 to 5 schematically depict the preparation of posterior triple tray 200 and making of a first impression 236 with first impression material 220 thereby producing a cured first impression 239 which later will be used for a second impression using second impression material 240.

FIG. 6 depicts a prepared tooth 246 which has been prepared to receive a crown thereon.

A tooth normally includes gum 254, roots 252, a gingival sulcus region 260, side surfaces 250 and a coronal or top portion 248.

FIG. 6 depicts the use of a light second impression material shown as 240 which preferably is a hydrophilic material and has a different color than first impression material 220 which normally is hydrophilic in nature and is of a different contrasting color.

Therefore first impression material 220 is hydrophilic and heavy meaning more viscous in nature and second impression material 240 is light meaning less viscous in nature and is a hydrophilic impression material and of a different color normally a contrast in color to first impression material 220.

Figure 3:
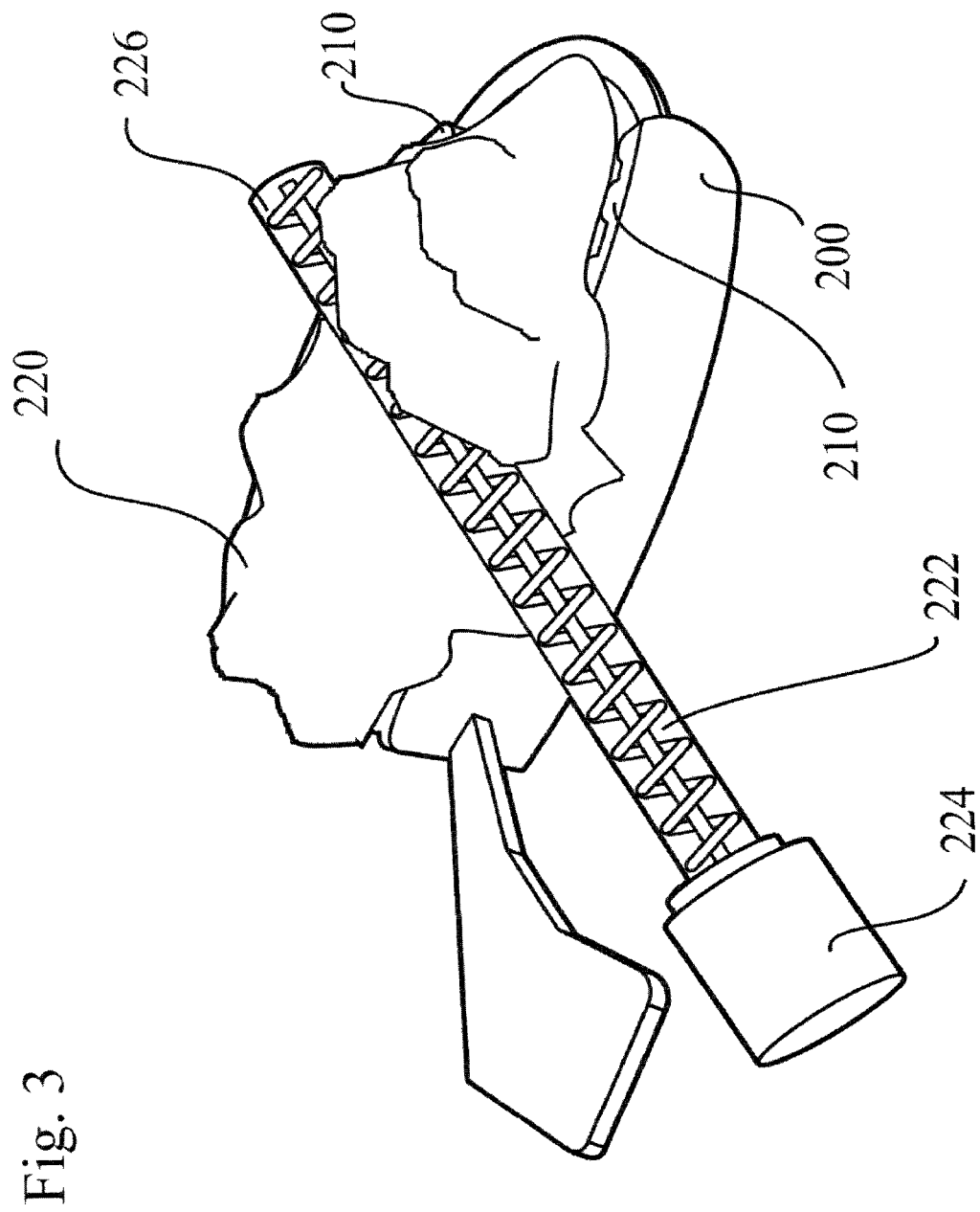
FIG. 3 is a schematic perspective top view of a posterior triple tray showing how the first impression material is being smoothed with the mixing nozzle.

Second impression material 240 is fed at an entry 242 through a mixing nozzle 256 and out through exit nozzle 244 and onto prepared tooth 246. Not shown in FIG. 6 nor in FIGS. 2 and 3 is the dual cartridges which deliver material to the entry end of mixing nozzle for the two part system of the vinyl polysiloxane.

Second impression material which is a hydrophilic vinyl polysiloxane having a light body meaning less viscous in texture than the first impression material 220.

The prepared tooth 246 is covered with a very light coating of second impression material 240 starting in the centre of the top coronal portion 248 of the prepared tooth 246 and working outwardly in circular motion as depicted in FIG. 6 to the outer diameter of prepared tooth 246.

Shown in FIG. 7 the user will then continue to apply light second impression 240 onto the crown side surface 250 of prepared tooth 246 and work from the top or the coronal portion 248 of the prepared tooth downwardly in the downwardly or gingival direction 258 until one reaches the gingival sulcus interface 260 in other words the gum-line or the gum 254 as depicted in FIG. 7.

This method of applying second impression material 240 is imperative in that any unwanted liquids including blood, saliva, water and other liquids that are unwanted are swept away by the light impression material 240 such that they do not later interfere with the second impression.

Figure 10:
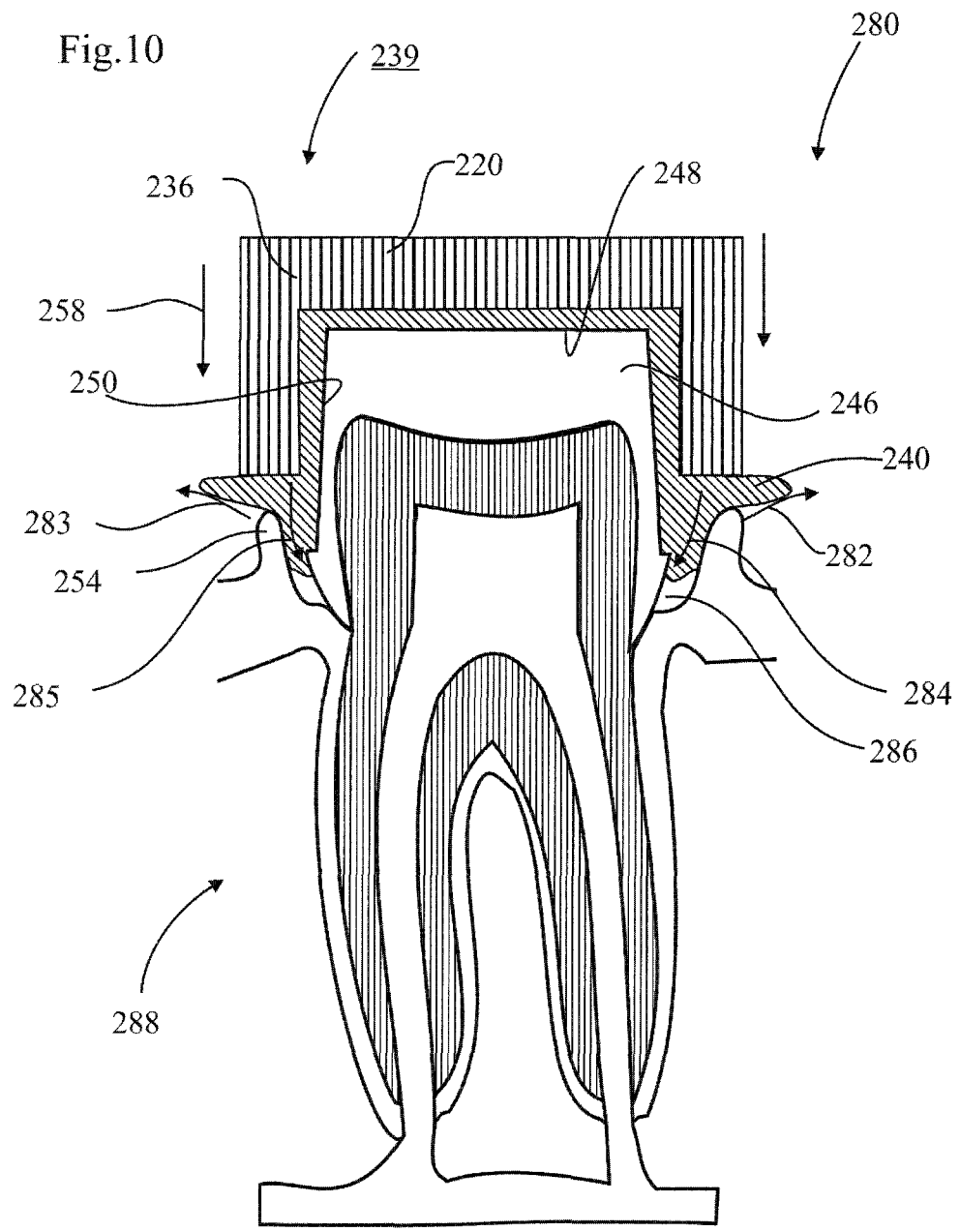
FIG. 10 is a schematic cross sectional plan view of a second impression being taken on a prepared tooth by placing the cured first impression over the prepared tooth covered with a second impression material showing the flow of second impression material into the gingival sulcus gap and thereby retracting the gingiva of the tooth.

Referring to FIG. 10, after the prepared tooth 246 has a light coating of second impression material 240 applied to it, the cured first impression 236 is manually positioned over the prepared tooth by the dentist and is urged downwardly 258 by the patient biting onto the posterior triple tray 200 thereby forcing second impression material 240 downwardly such that it is squeezed out of the gap between the first impression material 220 and the coronal portion 248 of the tooth and is downwardly ejected as shown as arrow 285 into the gingival sulcus gap 286 thereby creating hydraulic pressure in the direction as shown by arrow 284 creating gingival retraction 282 and lateral ejection of second impression material as shown in 283 thereby separating the gingiva or the gum from the tooth margin and any superfluous material is ejected laterally name shown as, lateral ejection arrow 283 out of the side until the bite is complete. Due to the viscosity and hydraulic pressure generated by the second impression material keeps fluid and blood from entering the sulcus until Step 2 is set.

Figure 11:
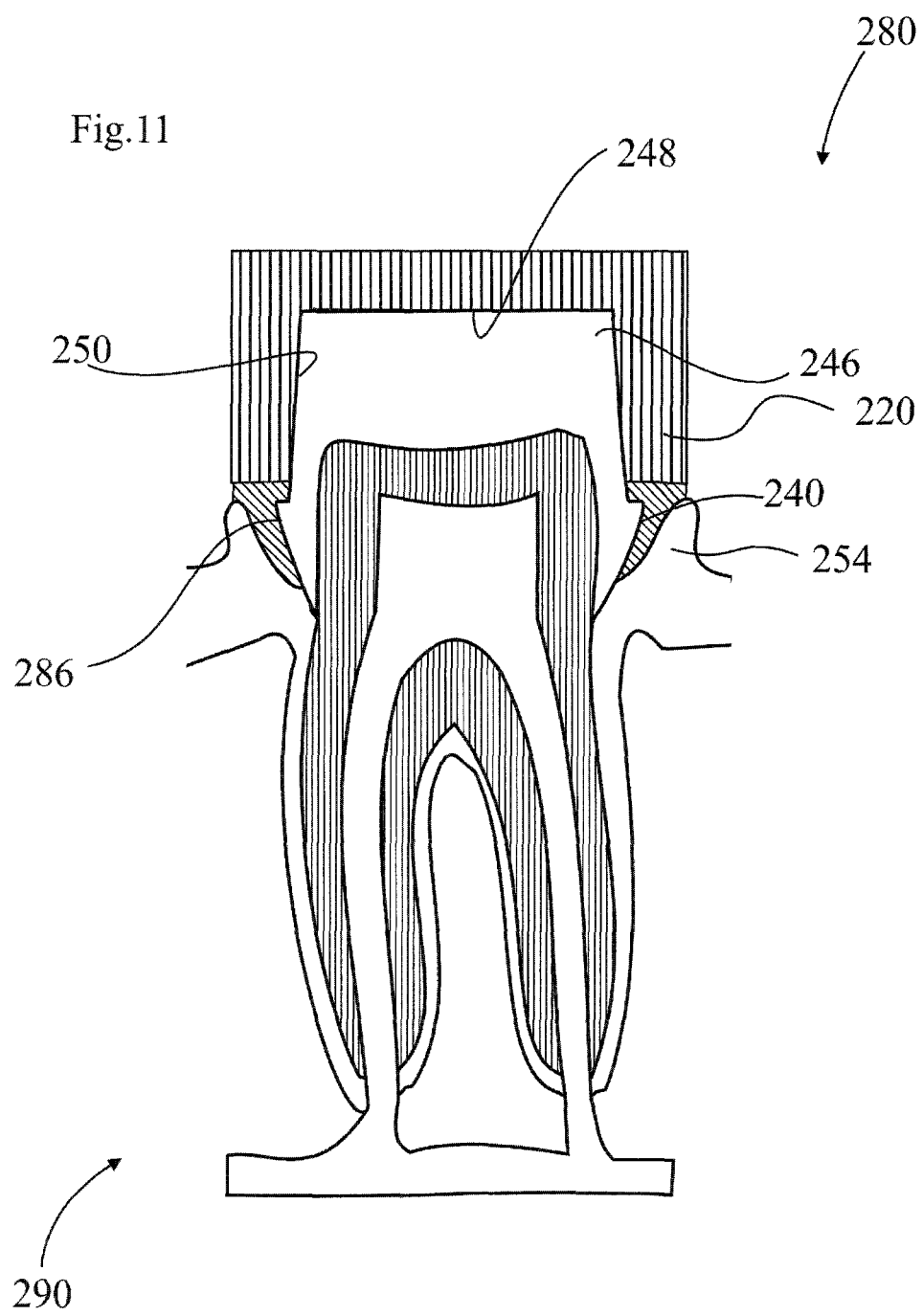
FIG. 11 is a schematic cross-sectional view of a prepared tooth showing a completed second impression of a prepared tooth with both the first impression material and the second impression material in positioned as it cures.

FIG. 10 shows the cured first impression 239 moving down into position forcing second impression material 240 to move downwardly along side surfaces 250 and eventually down into the sulcus gap 286 under hydraulic pressure 284 and ultimately any excess second impression material 240 is ejected laterally 283 during biting 288. FIG. 10 shows the biting not complexly bottomed whereas FIG. 11 shows the result after the bite has bottomed out. To best of the inventor's knowledge no other system utilizes hydraulic pressure in this manner nor is impression material applied directly to the prepared tooth as is here.

FIG. 11 is a schematic cross sectional view of a prepared tooth 246 showing a completed impression 290 wherein all of the excess second impression material 240 has been ejected either laterally as lateral ejection 282 shown in FIG. 10 or downwardly as downward ejection 285 shown in FIG. 10 such that the gingiva sulcus gap 286 has been filled with a second impression material due to the hydraulic pressure 284 of the second impression material 240.

In this manner it is not necessary to use a gingival retraction cord 270 as depicted in FIG. 9 since through the application of hydraulic pressure 284 one is able to obtain gingiva retraction 282 simply by making a second impression 280 as depicted in FIGS. 10 and 11. Additionally prior to making the step 2 impression it may be necessary to trace the sulcus of the tooth with an appropriate instrument such as an explorer or edged instrument to separate the sulcus from the tooth aiding the separation of the sulcus from the tooth with the application of hydraulic pressure.

FIG. 12 is a top perspective view of a completed impression. The person making the impression should view the impression to ensure that there is no second impression material 240 visible on the occlusal surfaces of the adjacent teeth shown as adjacent occlusal surface 296. Additionally one should observe that there is a thin wash second impression material 240 on the coronal impression 292 portion of the first impression 236 and one should observe only significant amounts of light second impression material 240 forming the gingiva sulcus impression 294 of the completed tooth impression 290 as shown in FIG. 12. One should also observe second impression material 240 being ejected laterally 283 from the prepared tooth as shown as 283 in FIG. 12. Additionally one should observe the structure of the impression and see fin like structures 295 in the sulcus area of the prepared tooth indicating the sulcus was retracted from the tooth through hydraulic pressure generated through the impression process.

Due to the contrast in colors between first impression material 220 and second impression material 240 one is able to visually detect and quite easily locate it where first impression material 220 is and where second impression material 240 has been left and cured.

There should be very little of second impression material 240 visible on any of the adjacent teeth and/or on the completed tooth except in the sulcus area of the tooth where it is desirable to have the second impression material 240.

Therefore one can take a quick visual check to ensure that the first and second impressions were properly carried out and therefore are depicting an accurate impression of the prepared tooth.

It should be apparent to persons skilled in the arts that various modifications and adaptation of this structure described above are possible without departure from the spirit of the invention the scope of which defined in the appended claim.

I claim:

1. A method of making a dental impression for use in making crowns, bridges, veneers and implants, the method comprising:
   a) providing an impression tray, a first high viscosity impression material, wherein the impression tray is filled with the first impression material;
   b) take a first impression by inserting the tray into the mouth over a prepared tooth for the patient to bite and let cure;
   c) remove the tray and apply a second low viscosity impression material over the prepared tooth and reinsert tray into the mouth over the prepared tooth of patient to bite and let cure to take a second impression of prepared tooth, wherein the hydraulic pressure created by the second impression material configured to urge the gingiva away from the tooth margin thereby causing gingival retraction; and
   d) remove the tray from the mouth of the patient, wherein the impression is configured for use in making crowns, bridges, veneers and implants.

2. The method claimed in claim 1 further including the step c' prior to step c as follows:
   c') tracing the sulcus of the prepared tooth with an instrument.

3. The method claimed in claim 1 further including the step c' prior to step c as follows:
   c') rinsing thoroughly the prepared tooth and tracing the sulcus of the prepared tooth with an instrument.

4. The method claimed in claim 1 further including the step e after the step d as follows:
   e) diagnose the quality of the impression.

5. The method claimed in claim 1 wherein in step c a layer of second impression material is applied over the prepared tooth starting at the coronal portion of the prepared tooth.

6. The method claimed in claim 1 wherein in step c a layer of second impression material is applied over the prepared tooth starting at the coronal portion of the prepared tooth and proceeding downwardly along the side surfaces of the tooth to the sulcus.

7. The method claimed in claim 1 wherein in step c a thin layer of second impression material is applied over the prepared tooth in a continuous circular motion starting at the coronal portion of the prepared tooth and proceeding downwardly around the side surfaces of the tooth to the sulcus.

8. The method claimed in claim 1 wherein in step a the first impression material is a hydrophilic polysiloxane impression material.

9. The method claimed in claim 1 wherein in step a the first impression material is a first colored impression material.

10. The method claimed in claim 1 wherein in step c the second impression material is a hydrophilic polysiloxane impression material.

11. The method claimed in claim 1 wherein in step c the second impression material is a second colored impression material.

12. The method claimed in claim 9 wherein in step c the second impression material is a second colored impression material contrasting with the first colored impression material.

13. The method claimed in claim 1 wherein in step a) the tray is a triple tray.

14. The method claimed in claim 1 wherein step c is replaced with the following step c' as follows:
   c') remove the tray and trim back excess first impression material and apply a second low viscosity impression material over the prepared tooth and reinsert tray into the mouth over the prepared tooth of patient to bite and let cure.

15. The method claimed in claim 12 wherein step c is replaced with the following step c' as follows:
   c') remove the impression tray and trim back excess first impression material to about ¼" above the top of the vertical walls of the impression tray and apply a second low viscosity impression material over the prepared tooth and reinsert tray into the mouth over the prepared tooth of patient to bite and let cure.

16. The method claimed in claim 4 wherein step e is replaced with the following step e) diagnose the quality of the impression by observing the colouring of the impression.

17. The method claimed in claim 4 wherein step e is replaced with the following step e) diagnose the quality of the impression by observing the colouring of the impression and reject the impression if second impression material is observed on any adjacent teeth.

18. The method claimed in claim 4 wherein step e is replaced with the following step e) diagnose the quality of the impression by observing the definition of the tooth impression.

19. The method claimed in claim 4 wherein step e is replaced with the following step e) diagnose the quality of the impression by observing the definition of the tooth impression and reject the impression if sharply defined fin like structures in the sulcus area of the prepared tooth are not present.

* * * * *